(12) United States Patent
Zhao et al.

(10) Patent No.: US 10,059,871 B2
(45) Date of Patent: *Aug. 28, 2018

(54) MULTI-TAIL HYDRATE INHIBITORS

(71) Applicant: Multi-Chem Group, LLC, San Angelo, TX (US)

(72) Inventors: Funian Zhao, Tomball, TX (US); Yanqui Sun, Houston, TX (US); Liangwei Qu, Spring, TX (US); Erick J. Acosta, Sugar Land, TX (US)

(73) Assignee: Multi-Chem Group, LLC, San Angelo, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/493,778

(22) Filed: Apr. 21, 2017

(65) Prior Publication Data

US 2017/0226403 A1    Aug. 10, 2017

Related U.S. Application Data

(62) Division of application No. 14/891,018, filed as application No. PCT/US2014/036747 on May 5, 2014, now Pat. No. 9,676,991.

(51) Int. Cl.
*C09K 8/52* (2006.01)
*C07C 233/36* (2006.01)

(52) U.S. Cl.
CPC .............. *C09K 8/52* (2013.01); *C07C 233/36* (2013.01); *C09K 2208/22* (2013.01)

(58) Field of Classification Search
CPC .. C09K 2208/22; C09K 8/52; C09K 2208/32; C09K 8/524; C09K 8/528; C09K 8/68; C09K 8/536; C09K 8/54; C09K 8/588; C09K 8/70; C09K 8/92; C09K 2208/10; C09K 3/18; C09K 8/035; C09K 8/04; C09K 8/516; C09K 8/5751; C09K 8/584; C09K 8/88; C09K 15/30; C09K 2208/18; C09K 2208/26; C09K 2208/34; C09K 5/20; C09K 8/00; C09K 8/03; C09K 8/44; C09K 8/487; C09K 8/506; C09K 8/508; E21B 37/06; E21B 43/01; E21B 43/0122; E21B 43/16; E21B 2021/005; E21B 21/001; E21B 21/08; E21B 33/138; E21B 41/0007; E21B 7/00; E21B 2043/0115; E21B 33/13; E21B 43/025; E21B 43/25

See application file for complete search history.

(56) References Cited

U.S. PATENT DOCUMENTS

| | | | |
|---|---|---|---|
| 3,492,324 A * | 1/1970 | Blackman | D06M 13/405 252/8.63 |
| 8,329,620 B2 | 12/2012 | Acosta | |
| 2006/0237691 A1 | 10/2006 | Meier et al. | |
| 2008/0064611 A1 | 3/2008 | Spratt | |
| 2012/0078021 A1 | 9/2012 | Durham et al. | |
| 2014/0094393 A1 | 4/2014 | Webber | |
| 2015/0191645 A1* | 7/2015 | Levey | C09K 8/52 507/90 |

FOREIGN PATENT DOCUMENTS

WO    2013-053770 A1    4/2013

OTHER PUBLICATIONS

International Search Report and Written Opinion issued in related PCT Application No. PCT/US2014/036747, dated Feb. 2, 2015 (10 pages).

* cited by examiner

*Primary Examiner* — Kumar R Bhushan
(74) *Attorney, Agent, or Firm* — Tenley Krueger; Baker Botts L.L.P.

(57) ABSTRACT

Low-dosage hydrate inhibitor ("LDHI") compounds comprising multiple lipophilic tails and a hydrophilic head may be employed into fluids to inhibit agglomeration of hydrates, among other things. Suitable hydrophilic heads may include quaternary or tertiary ammonium cation moieties, and combinations thereof. Such LDHI compounds in some embodiments may include reaction products of DETA and/or other amines, fatty acid(s), and, optionally, alkyl halide(s). Compounds according to some embodiments may be employed in fluids in various environments, such as a conduit penetrating a subterranean formation, or a conduit carrying fluid in an industrial setting.

11 Claims, 3 Drawing Sheets

MULTI-TAIL HYDRATE INHIBITORS

CROSS REFERENCE TO RELATED APPLICATIONS

This application is a divisional application of U.S. application Ser. No. 14/891,018 entitled "Multi-Tail Hydrate Inhibitors," filed Nov. 13, 2015, now U.S. Pat. No. 9,676,991, which is a U.S. National Stage Application of International Application No. PCT/US2014/036747 filed May 5, 2014, each which is herein incorporated by reference in its entirety.

BACKGROUND

The present disclosure relates generally to compounds useful in processes involving fluid flowing through, or contained in, conduits such as pipes, such as the production of petroleum products, natural gas, and the like. More particularly, the present disclosure relates to compositions and the use of such compositions, such as in the inhibition of the formation of gas hydrate agglomerates.

Gas hydrates are solids that may agglomerate in a fluid that is flowing or is substantially stationary, under certain temperature and pressure conditions. For example, gas hydrates may form during hydrocarbon production from a subterranean formation, in particular in pipelines and other equipment during production operations. Hydrates may impede or completely block flow of hydrocarbons or other fluid flowing through such pipelines. These blockages not only may decrease or stop production, potentially costing millions of dollars in lost production, but also may be very difficult and dangerous to mediate. Unless properly handled, gas hydrates may be volatile and/or explosive, potentially rupturing pipelines, damaging equipment, endangering workers, and/or causing environmental harm.

Gas hydrates may form when water molecules become bonded together after coming into contact with certain "guest" gas or liquid molecules. Hydrogen bonding causes the water molecules to form a regular lattice structure, like a cage, that is stabilized by the guest gas or liquid molecules entrapped within the lattice structure. The resulting crystalline structure may precipitate as a solid gas hydrate. Guest molecules can include any number of molecules such as, for example, carbon dioxide, methane, butane, propane, hydrogen, helium, freon, halogen, a noble gas, and the like.

While embodiments of this disclosure have been depicted and described and are defined by reference to certain embodiments, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and are not exhaustive of the scope of the disclosure.

DETAILED DESCRIPTION

Illustrative embodiments of the present disclosure are described in detail herein. In the interest of clarity, not all features of an actual implementation may be described in this specification. It will of course be appreciated that in the development of any such actual embodiment, numerous implementation-specific decisions may be made to achieve the specific implementation goals, which may vary from one implementation to another. Moreover, it will be appreciated that such a development effort might be complex and time-consuming, but would nevertheless be a routine undertaking for those of ordinary skill in the art having the benefit of the present disclosure.

To facilitate a better understanding of the present disclosure, the following examples of certain embodiments are given. In no way should the following examples be read to limit, or define, the scope of the invention. Embodiments of the present disclosure may be applicable to horizontal, vertical, deviated, or otherwise nonlinear wellbores in any type of subterranean formation. Embodiments may be applicable to injection wells, monitoring wells, and production wells, including hydrocarbon or geothermal wells.

Hydrate inhibitors are often grouped into 3 general classes: thermodynamic, anti-agglomerate, and kinetic hydrate inhibitors. Thermodynamic inhibitors are believed to operate by shifting the hydrate formation phase boundary away from temperature and pressure conditions of a process by increasing the driving force required for formation of the hydrate. Such inhibitors may require high concentrations to be effective (e.g., up to 50% or 60% inhibitor by amount of water). Kinetic inhibitors and anti-agglomerate inhibitors may function at lower concentrations than thermodynamic inhibitors, and therefore may be termed low dosage hydrate inhibitors (LDHIs). Kinetic hydrate inhibitors may prevent or delay the nucleation of hydrates, thus limiting hydrate crystal size and growth. Anti-agglomerate LDHIs are believed to prevent or otherwise disrupt the agglomeration of hydrates.

The present disclosure relates generally to compounds useful in processes involving fluid flowing through, or contained in, conduits such as pipes, such as the production of petroleum products, natural gas, and the like. More particularly, the present disclosure relates to compositions and the use of such compositions, such as in the inhibition of the formation of gas hydrate agglomerates.

In some embodiments, the present disclosure may provide a low-dosage hydrate inhibitor (LDHI) compound comprising multiple lipophilic tails, a hydrophilic head, and a linking moiety. In some aspects, the present disclosure may also or instead provide salts of such compounds. The present disclosure further provides methods of using such compounds and/or salts thereof to inhibit the formation of one or more hydrates in a fluid. For example, some embodiments provide a method of inhibiting the formation of hydrate agglomerates in a fluid comprising any one or more of water, gas, hydrocarbons, and combinations thereof. Such a method could include adding to the fluid an effective amount of a composition comprising a compound according to the present disclosure, and/or salts thereof.

Among the many advantages provided herein, compounds and methods of using compounds according to the present disclosure may provide enhanced anti-agglomeration properties. For example, referring to embodiments relating to methods for inhibiting the formation of hydrate agglomerates: hydrate agglomeration may be inhibited to a greater degree than that using conventional means, and/or a smaller quantity of LDHI may inhibit hydrate agglomeration. In particular embodiments, compounds of the present disclosure may provide enhanced inhibition of agglomeration of hydrates and/or hydrate-forming compounds.

The lipophilic tails according to some embodiments may each independently comprise a $C_1$ to $C_{50}$ hydrocarbon chain. As used herein, a "hydrocarbon chain" may, unless otherwise specifically noted, be substituted or unsubstituted (that is, it may or may not contain one or more additional moieties or functional groups in place of one or more hydrogens in the hydrocarbon chain); it may be branched, unbranched, acyclic, and/or cyclic; and/or it may be saturated or unsaturated. Furthermore, as used herein, the nomenclature "$C_x$ to $C_y$," refers to the number of carbon atoms in the hydrocarbon chain (here, ranging from x to y carbon atoms).

A hydrocarbon chain on a lipophilic tail may be branched or unbranched, cyclic or non-cyclic, and may be any one or more of alkyl, alkenyl, alkynyl, and aryl groups, and/or combinations thereof. A lipophilic tail may further optionally be substituted with any one or more additional groups, so long as such substituted additional group or groups do not alter the lipophilic and/or hydrophobic nature of the tail. In particular embodiments, a lipophilic tail may comprise (i) as few as any one of: 1, 2, 3, 4, 5, 6, 7, 8, 9, 10, 11, 12, 13, 14, 15, 16, 17, 18, 19, and 20 carbons, and (ii) as many as any one of: 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, and 50 carbons. For example, suitable ranges of carbon atoms in the tail according to various embodiments include: 1 to 5, 3 to 5, 4 to 8, 5 to 15, 8 to 18, 12 to 16, 8 to 20, 10 to 20, 15 to 20, etc. In some embodiments, a lipophilic tail may be of identical composition to any one or more other lipophilic tails of the compound. In other embodiments, each lipophilic tail may be of different composition than any one or more other lipophilic tails.

Figure 1:
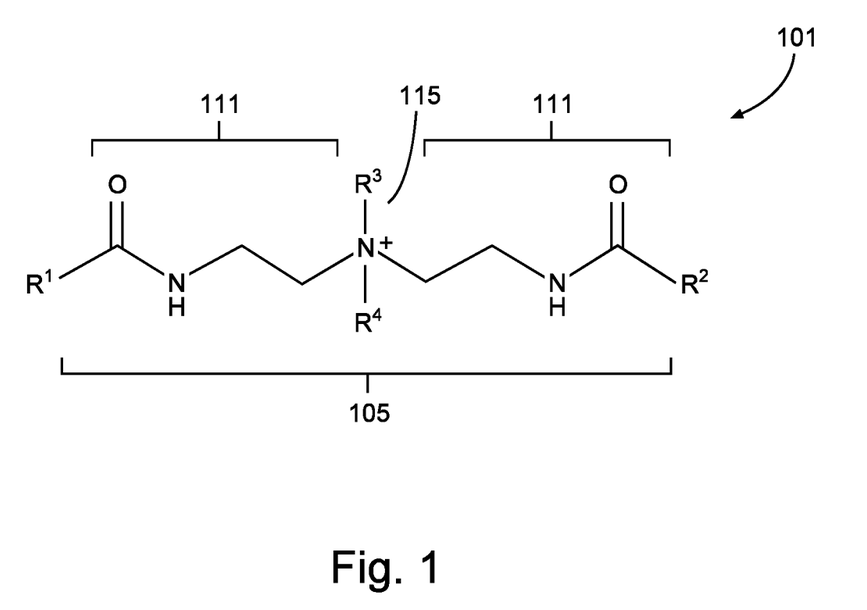
FIG. 1 is a diagram illustrating a compound that includes multiple lipophilic tails and a quaternary ammonium cation moiety in accordance with aspects of the present disclosure.

In some embodiments, at least two of the lipophilic tails of the compound are located at end-points of the compound. For example, as shown in FIG. 1, example LDHI compound 101 comprises two lipophilic tails $R^1$ and $R^2$, each located at end-points of the compound 101. It will be appreciated by one of ordinary skill in the art that even in such embodiments, additional lipophilic tails could be included in the compound (e.g., at a point along the backbone 105 of the compound 101 linking the two lipophilic tails $R^1$ and $R^2$ together).

LDHI compounds of the present disclosure may further comprise a hydrophilic head. In some embodiments, a hydrophilic head may comprise a cation moiety. In particular embodiments, a hydrophilic head may comprise a cation moiety selected from the group consisting of: quaternary ammonium cation moieties and tertiary ammonium cation moieties. Such a cation moiety may be embedded within the compound (that is, bonded in two locations to other moieties of the compound), such as is shown with respect to hydrophilic head 115 of the compound 101 in FIG. 1. Thus, the cation moiety may be substantially of the composition—$R^3R^4N^+$—. Each of $R^3$ and $R^4$ may comprise an organic moiety, such as a hydrocarbon chain comprising any one or more of: alkyl, alkenyl, alkynyl, aryl, arylalkyl, arylalkenyl, alkylaryl, alkenylaryl, glycol, and combinations thereof. Each of $R^3$ and $R^4$ may be branched or linear. Each R-group may be different, although in some embodiments the two R-groups of a cation moiety may be identical. In particular embodiments wherein the cation moiety is a tertiary ammonium cation moiety, any one of R-groups $R^3$ and $R^4$ may be H. Some embodiments may further include a secondary ammonium cation moieties. In such embodiments, both of $R^3$ and $R^4$ may be H. Nonetheless, in certain other embodiments, only one of $R^3$ and $R^4$ may be H (that is, in certain embodiments the cation moiety must be a tertiary or quaternary ammonium).

Where any one or more R-group is not H, each R-group may be a $C_1$ to $C_{20}$ hydrocarbon chain (excepting embodiments wherein the R-group comprises an alkenyl or alkynyl group, in which case at least 2 carbon atoms are necessary), or in other embodiments a $C_2$ to $C_6$ hydrocarbon chain, or in other embodiments a $C_3$ to $C_6$, or $C_4$ to $C_8$, hydrocarbon chain. Thus, an R-group of some embodiments may comprise a $C_1$ to $C_{10}$ alkyl chain, or in other embodiments a $C_2$ to $C_6$ alkyl, alkenyl, or alkynyl chain (branched or unbranched), or in yet other embodiments a $C_3$ to $C_6$ alkyl, alkenyl, or alkynyl chain (branched or unbranched). Similarly, an R-group may comprise a $C_3$ to $C_{10}$ aryl moiety (and likewise for $C_3$ to $C_6$ moieties). Some embodiments may include R-groups of smaller alkyl, alkenyl, alkynyl, or aryl groups, such as a group having at least 1 but not more than 5, 4, 3, or 2 carbon atoms, in respective embodiments (with the above-mentioned caveats for alkenyl, alkynyl, and/or aryl groups). A hydrocarbon chain of an R-group according to various embodiments may be either substituted or unsubstituted, and/or branched or unbranched, cyclic or non-cyclic. An R-group according to some embodiments may be substituted (e.g., it may include other groups in addition to the hydrocarbon groups described above), so long as the cation moiety remains hydrophilic.

In certain embodiments, each R-group of a cation moiety may be smaller (e.g., contain fewer carbon atoms) than either of the lipophilic tails of the compound.

The compounds of some embodiments may further include one or more linking moieties. A linking moiety is any portion of the compound that provides spacing between a hydrophilic head and lipophilic tail. In some embodiments, the compound may comprise one linking moiety for each lipophilic tail, each linking moiety providing spacing between the corresponding lipophilic tail and a hydrophilic head. In particular embodiments, each of two or more lipophilic tails may each be separated from a single hydrophilic head by each of two or more linking moieties, each linking moiety being bonded to the hydrophilic head. Returning for instance to the compound 101 shown in FIG. 1, the hydrophilic head 115 is separated from the first lipophilic tail $R^1$ by linking moiety 111, and from the second lipophilic tail $R^2$ by linking moiety 112. In some embodiments, a linking moiety may provide sufficient spacing so that the compound overall maintains amphiphilic character. A linking moiety may comprise any length hydrocarbon chain, branched or unbranched, again so long as the overall compound maintains amphiphilic character. Hydrocarbon chain lengths include $C_1$ to $C_{50}$ chains or longer. For instance, a linking group may be any one or more of methyl, ethyl, propyl, butyl, pentyl, hexyl, heptyl, octyl, nonyl, decyl, etc. Furthermore, a linking moiety may include any kind and number of functional groups, again so long as the compound maintains both hydrophobic and hydrophilic portions. Further, a functional group included on a linking moiety according to some embodiments should not adversely affect the hydrophilic nature of a hydrophilic head, nor should it adversely affect the lipophilic nature of a lipophilic tail. Suitable functional groups that may be included in a linking moiety according to some embodiments may include any one or more of: an ester, sulfona- mide, amide, ketone, carbonyl, isocyanate, urea, urethane, and combinations thereof. In some instances, a functional group on a linking group may include any group capable of reacting with an amine, again so long as that functional group's inclusion in the linking group allows the compound to maintain amphiphilic character. The compound 101 of FIG. 1 includes examples of linking moieties 111, each comprising an amide and a carbonyl group, as well as an ethyl group.

LDHI compounds according to embodiments of the present disclosure may instead or in addition be characterized as reaction products. For instance, in some embodiments, the present disclosure provides a compound that may be characterized as the reaction product of: (1) an amide intermediate resulting from reaction between DETA (diethylenetriamine) and a stoichiometric amount of any one or more kinds of fatty acids; and (2) alkyl halide. Compounds according to such embodiments will typically include a hydrophilic head comprising a quaternary ammonium cation. The R-group(s) of the quaternary ammonium cation may depend upon the identity of the alkyl halide used. Similarly, the composition of the lipophilic tails of such compounds may depend upon the fatty acid(s) used. In particular embodiments, a fatty acid may lead to a mixture of different-length lipophilic tails in a single molecule of a compound, and/or as between two or more different molecules of the compound. In addition, a portion of a functional group of the fatty acid(s) may be included in the linking moiety of the resultant reactant product. Suitable fatty acids for reaction may include a saturated fatty acid and/or an unsaturated fatty acid, such as one or more selected from the group consisting of: corn oil, canola oil, coconut oil, safflower oil, sesame oil, palm oil, cottonseed oil, soybean oil, olive oil, sunflower oil, hemp oil, wheat germ oil, palm kernel oil, vegetable oil, caprylic acid, capric acid, lauric acid, stearic acid, myristic acid, myristoleic acid, palmitic acid, palmitoleic acid, stearic acid, sapienic acid, elaidic acid, vaccenic acid, linoleic acid, arachidic acid, arachidonic acid, eicosapentaenoic acid, erucic acid, docosahexaenoic acid, behenic acid, lignoceric acid, cerotic acid, oleic acids (cis- and trans-), and combinations thereof.

Figure 2:
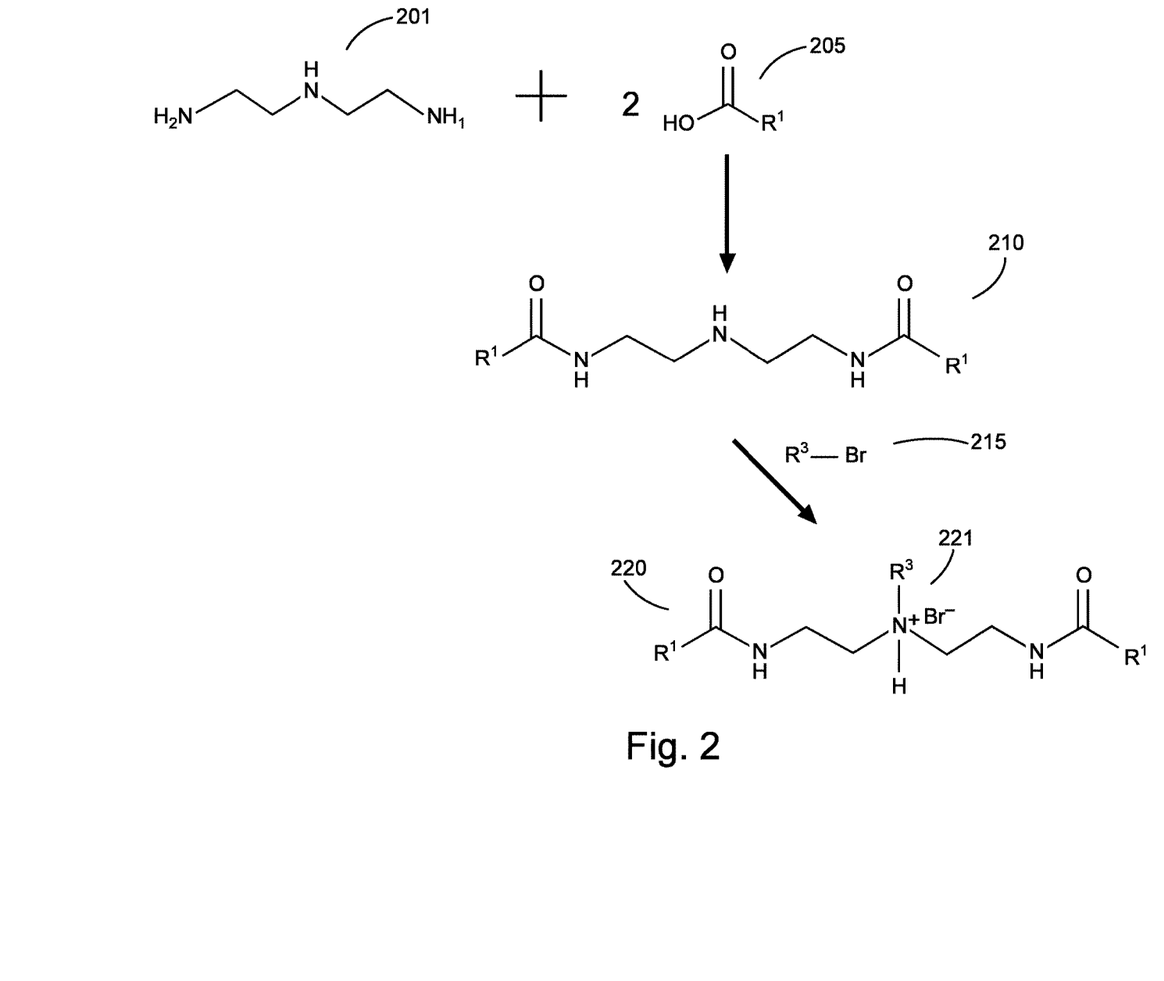
FIG. 2 is a diagram illustrating an example reaction process in accordance with aspects of the present disclosure.

The reaction scheme of FIG. 2 illustrates an example of a compound (and its formation) according to some such embodiments. In the reaction scheme shown, 1 mole of DETA 201 reacts with 2 moles of fatty acid 205 (which, as shown in FIG. 2, comprises hydrocarbon chain $R^1$), forming the amide intermediate 210. The amide intermediate 210 in turn reacts with alkyl halide 215 (comprising $R^3$ as shown in FIG. 2) to form the LDHI compound 220. As can be seen, LDHI compound 220 includes two lipophilic tails $R^1$ (each retaining the hydrocarbon structure $R^1$ of the fatty acid) and a hydrophilic head 221 comprising an R-group $R^3$ (retaining the hydrocarbon structure $R^3$ of the alkyl halide). Such reactions may in some embodiments take place at about 80 to about 120° C. at approximately atmospheric pressure. It will be appreciated by one of ordinary skill in the art that various modifications may be made to this reaction scheme to produce other embodiments. For example, a mixture of two types of fatty acids comprising hydrocarbon chains $R^1$ and $R^2$, respectively, could be used in the first reaction step, whereupon the amide intermediate (and therefore resulting LDHI compound) may include a mixture of amides: some comprising two lipophilic tails, each having structure $R^1$; some comprising two lipophilic tails each having structure $R^2$; and some comprising two lipophilic tails of mixed structure (e.g., one $R^1$ and one $R^2$). Furthermore, in yet other embodiments, another reactant besides fatty acid may be used. Examples of other reactants include: esters, sulfonamides, amides, ketones, carbonyls, isocynates, urea, urethane, and combinations thereof.

In some embodiments, the present disclosure may instead or in addition provide salts of compounds as described herein. For example, the reaction product 220 as shown in FIG. 2 comprises a salt with a bromide ion. Such salts may wholly or partially dissociate in aqueous solution. In other embodiments, the salts may remain substantially associated (either with the original anion or with other ions from solution). It will be appreciated by one of ordinary skill in the art with the benefit of this disclosure that salts may be formed with other anions instead of or in addition to chloride anions. For instance, suitable anions may comprise any one or more of hydroxide, carboxylate, halide, sulfate, organic sulfonate, and combinations thereof.

In some embodiments, LDHI compounds may be characterized as multi-tail, multi-amino organic compounds. For instance, compounds according to such embodiments may have substantially the following structural formula:

Each of $R^1$ and $R^2$ may be a hydrocarbon chain according to previous discussion of lipophilic tails $R^1$ and $R^2$ (e.g., each may be a $C_1$ to $C_{50}$ hydrocarbon chain, etc.).

Each of Z and Z' may be moieties that comprise one or more functional groups and/or carbon chains independently comprising esters, carbonyls, isocyanates, carbonyl amides, sulfonamides, sulfonates, esters, ethers, and combinations thereof. In certain embodiments, the carbonyl amides may comprise a urea or urethane. In certain embodiments, each of Z and Z' may comprise any functional group capable of reacting with an amine, but the inclusion of which in the compound maintains the hydrophobicity of each of $R^1$ and $R^2$.

Each of L and L' may be a $C_1$ to $C_{20}$ hydrocarbon chain. In certain embodiments, either or both of L and L' may be unsubstituted. In other embodiments, either or both may be substituted.

In particular embodiments, the moieties Z—NH-L and L'-NH—Z' may each be characterized as a linking group, and may in the aggregate be any linking group in accordance with linking groups previously discussed herein.

M may be an amine or an ammonium cation moiety. In particular, M may be selected from the group consisting of $R^3N$ and $R^3R^4N^+$, wherein each of $R^3$ and $R^4$ may independently be selected from the group consisting of: hydrogen and a $C_1$ to $C_{10}$ hydrocarbon chain. Each of $R^3$ and $R^4$ in some embodiments may be in accordance with $R^3$ and $R^4$ discussed previously with respect to a cationic hydrophilic head. In embodiments wherein M is $R^3R^4N^+$, that moiety may be associated (e.g., ionically bonded or otherwise associated) with an anion X, such that the compound has the structural formula shown below:

X may be selected from the group consisting of halide, carboxylate, sulfate, organic sulfonate, hydroxide, and combinations thereof.

In certain embodiments, each one of the moieties $R^1$—Z and Z'—$R^2$ may collectively be characterized as a moiety resulting from reaction between an amine and a fatty acid. In such embodiments, Z and Z' are each a carbonyl, and $R^1$ and $R^2$ each may be any hydrocarbon chain resulting from reaction of the amine groups having structure $H_2N$-L-NH-L'-$NH_2$ and the fatty acid or fatty acids. Thus, for example, each of $R^1$ and $R^2$ in such embodiments may be a hydrocarbon chain resulting from reaction of (i) an amine having the structure $H_2N$-L-NH-L'-$NH_2$ and (ii) a fatty acid selected from the group consisting of: corn oil, canola oil, coconut oil, safflower oil, sesame oil, palm oil, cottonseed oil, soybean oil, olive oil, sunflower oil, hemp oil, wheat germ oil, palm kernel oil, vegetable oil, caprylic acid, capric acid, lauric acid, stearic acid, myristic acid, myristoleic acid, palmitic acid, palmitoleic acid, stearic acid, sapienic acid, elaidic acid, vaccenic acid, linoleic acid, arachidic acid, arachidonic acid, eicosapentaenoic acid, erucic acid, docosahexaenoic acid, behenic acid, lignoceric acid, cerotic acid, oleic acids (cis- and trans-), and combinations thereof. It should be noted that such embodiments may include M as either $R^3N$ or $R^3R^4N^+$, because (as described previously) the reaction product of amine and fatty acid may be further reacted (e.g., with alkyl halide) to quaternize the central amine, but it need not necessarily be so reacted. Either way, this latter reaction of such embodiments may be carried out such that it does not affect the identity of $R^1$ and $R^2$ resulting from the former reaction between amine and fatty acid.

Compounds including multiple lipophilic tails and one or more hydrophilic heads according to the foregoing, and/or their salts, may be surfactants, and/or may have surfactant-like properties (such as amphiphilic qualities).

As previously noted, the present disclosure in some embodiments further provides methods of using compounds according to the present disclosure to inhibit the formation of one or more hydrates. Thus, the present disclosure may provide a method of inhibiting the formation of one or more hydrates in a fluid comprising any one or more of water, gas, liquid hydrocarbon, and combinations thereof, the method comprising adding to the fluid an effective amount of an LDHI compound according to the present disclosure. The LDHI compound may comprise multiple hydrophilic heads, a lipophilic tail, and a linking group, in accordance with compounds discussed with respect to various embodiments herein. The fluid may be flowing or it may be substantially stationary. In some instances, the fluid may be in a high-pressure, low-temperature environment.

Some embodiments may include introducing a composition comprising an LDHI compound as described herein (e.g., a compound that includes multiple hydrophilic heads, a lipophilic tail, and a linking group), and/or a salt of such a compound, to a fluid comprising water and any one or more of gas, liquid hydrocarbon, and combinations thereof. Although listed separately from liquid hydrocarbon, the gas may in some embodiments include gaseous hydrocarbon, though the gas need not necessarily include hydrocarbon. The composition may be any suitable composition in which the LDHI compound may be included. For example, in some embodiments, the composition may be a treatment fluid for use in a wellbore penetrating a subterranean formation during, for instance, oil and/or gas recovery operations. The composition may include a solvent for the LDHI compound. Suitable solvents include any one or more of: toluene, xylene, methanol, isopropyl alcohol, any alcohol, glycol, any organic solvent, and combinations thereof. The fluid may be within a vessel, or within a conduit (e.g., a conduit that may transport the fluid), or within a wellbore and/or a subterranean formation. Examples of conduits include, but are not limited to, pipelines, production piping, subsea tubulars, process equipment, and the like as used in industrial settings and/or as used in the production of oil and/or gas from a subterranean formation, and the like. The conduit may in certain embodiments penetrate at least a portion of a subterranean formation, as in the case of an oil and/or gas well. In particular embodiments, the conduit may be a wellbore or may be located within a wellbore penetrating at least a portion of a subterranean formation. Such oil and/or gas well may, for example, be a subsea well (e.g., with the subterranean formation being located below the sea floor), or it may be a surface well (e.g., with the subterranean formation being located belowground). A vessel or conduit according to other embodiments may be located in an industrial setting such as a refinery (e.g., separation vessels, dehydration units, pipelines, heat exchangers, and the like), or it may be a transportation pipeline.

Methods according to some embodiments may further include allowing the LDHI compound to concentrate at an oil-water interface in the fluid (e.g., an interface between water and gas in the fluid, and/or between water and liquid hydrocarbon).

The compound in some embodiments may be introduced in an amount equal to about 0.1 to about 5.5% volume based on water in the fluid (or in other words, about 0.1% to about 3.0% volume based on water cut). In various embodiments, an effective amount of compound for inhibiting hydrates may be as low as any of: 0.1, 0.25, 0.50, 0.75, 1.00, 1.25, 1.50, 1.75, 2.00, 2.25, and 2.50% volume based on water cut. An effective amount may be as high as any of: 0.50, 0.75, 1.00, 1.25, 1.50, 1.75, 2.00, 2.25, 2.50, 2.75, 3.00, 3.25, 3.50, 3.75, 4.00, 4.50, 5.00, and 5.50% volume based on water cut. Thus, in particular embodiments, an effective amount of compound for inhibiting agglomeration of hydrates may be about 0.1 to about 3% volume based on water cut of the fluid; in other embodiments, about 0.1 to about 2% volume; in further embodiments, about 0.25 to about 1.5% volume; and in yet other embodiments, about 0.5 to about 1.0% volume.

Furthermore, the compound in certain embodiments may be introduced to any of various fluids having different water cuts. For example, in some embodiments the water cut may be about 30 to about 50%. In other embodiments, the water cut may be as low as any one of: 20, 25, 30, 35, 40, 45, and 50%; while the water cut may be as high as any one of: 35, 40, 45, 50, 55, 60, 65, 70, 75, 80, 85, 90, and 95%. In certain embodiments, a fluid may have a water cut of 50% or more, 40% or more, or 30% or more, up to about 99%. In yet other embodiments, an LDHI compound may be used in a fluid with any water cut ranging from about 1% to about 99%.

The hydrate inhibitors of the present disclosure may be introduced into a well bore, subterranean formation, vessel, and/or conduit (and/or to a fluid within any of the foregoing) using any method or equipment known in the art. For example, these hydrate inhibitors may be applied to a subterranean formation and/or well bore using batch treatments, squeeze treatments, continuous treatments, and/or combinations thereof. In certain embodiments, a batch treatment may be performed in a subterranean formation by stopping production from the well and pumping the dissolved hydrate inhibitors into a well bore, which may be performed at one or more points in time during the life of a well. In other embodiments, a squeeze treatment may be performed by dissolving the hydrate inhibitor in a suitable solvent at a suitable concentration and squeezing that solvent carrying the hydrate inhibitor downhole into the formation, allowing production out of the formation to bring the hydrate inhibitor to its desired location. In still other embodiments, a hydrate inhibitor of the present disclosure may be injected into a portion of a subterranean formation using an annular space or capillary injection system to continuously introduce the hydrate inhibitor into the formation. In certain embodiments, a composition (such as a treatment fluid) comprising a hydrate inhibitor of the present disclosure may be circulated in the well bore using the same types of pumping systems and equipment at the surface that are used to introduce treatment fluids or additives into a well bore penetrating at least a portion of the subterranean formation.

Figure 3:
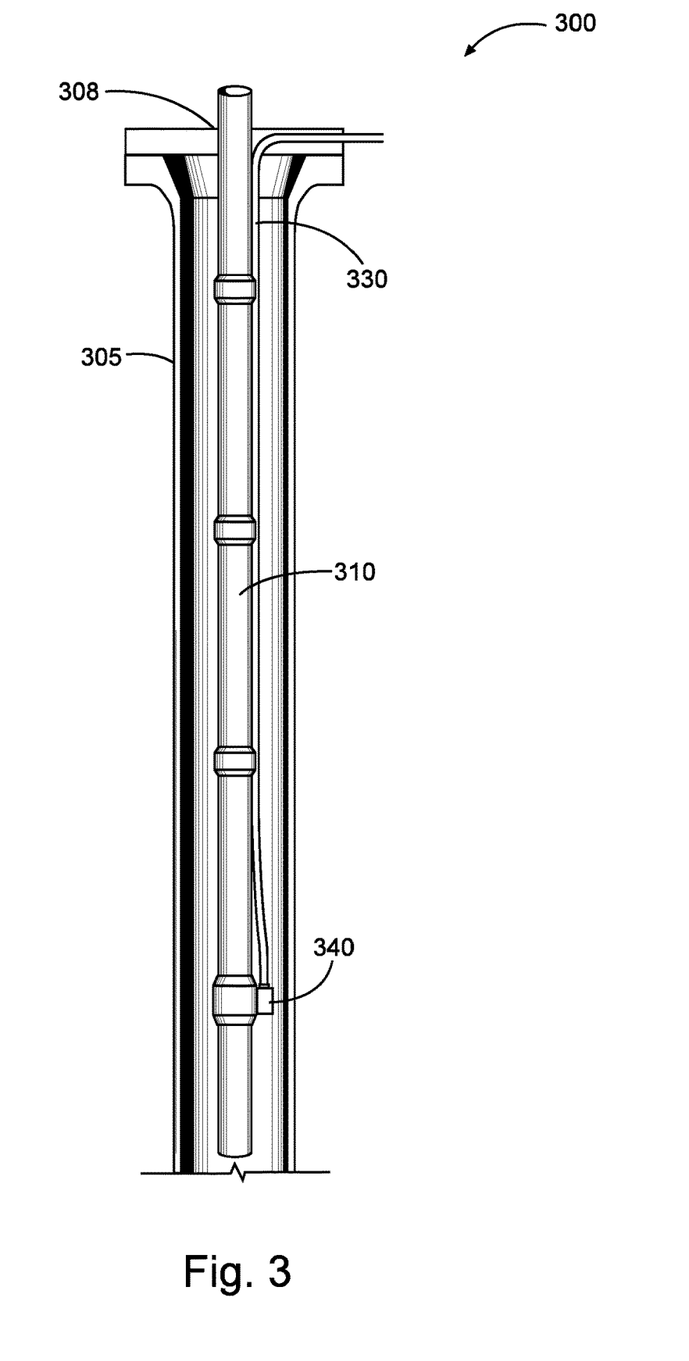
FIG. 3 is a diagram illustrating an injection system that may be used in accordance with certain embodiments of the present disclosure.

For example, a hydrate inhibitor of the present disclosure may be introduced into a well bore and/or tubing using a capillary injection system as shown in FIG. 3. Referring now to FIG. 3, well bore 305 has been drilled to penetrate a portion of a subterranean formation 300. A tubing 310 (e.g., production tubing) has been placed in the well bore 305. A capillary injection tube 330 is disposed in the annular space between the outer surface of tubing 310 and the inner wall of well bore 305. The capillary injection tube 330 is connected to a side-pocket mandrel 340 at a lower section of the tubing 310. A hydrate inhibitor may be injected into capillary injection tube 330 at the wellhead 308 at the surface such that it mixes with production fluid at or near the side-pocket mandrel 340. As the production fluid flows through the tubing 310, the hydrate inhibitors may prevent the formation of one or more hydrates within the tubing 310. Other capillary injection systems and side pocket mandrel devices (e.g., those used in gas lift production) may be used in a similar manner to the system shown in FIG. 3.

In certain embodiments, a hydrate inhibitor of the present disclosure may be added to a conduit such as a pipeline where one or more fluids enter the conduit and/or at one or more other locations along the length of the conduit. In these embodiments, the hydrate inhibitor may be added in batches or injected substantially continuously while the pipeline is being used.

Once introduced into a fluid, subterranean formation, well bore, pipeline, or other location, the hydrate inhibitor may inhibit the formation of one or more hydrates within the fluid, subterranean formation, well bore, pipeline, or other location.

In a first embodiment, the present disclosure may provide a method of inhibiting the formation of hydrate agglomerates, the method comprising: introducing a composition into a fluid comprising (i) water and (ii) one of gas, liquid hydrocarbon, and combinations thereof; wherein the composition comprises an LDHI compound, the LDHI compound having the structural formula:

Each of $R^1$ and $R^2$ is a $C_1$ to $C_{50}$ hydrocarbon chain; each of Z and Z' is a functional group capable of reacting with an amine, the inclusion of which maintains hydrophobicity of each of $R^1$ and $R^2$; each of L and L' is a $C_1$ to $C_{20}$ hydrocarbon chain; and M is selected from the group consisting of $R^3N$ and $R^3R^4N^+$, wherein each of $R^3$ and $R^4$ may independently be selected from the group consisting of: hydrogen and a $C_1$ to $C_{10}$ hydrocarbon chain.

In a second embodiment, the present disclosure may provide a method according to the first embodiment, wherein each of Z and Z' may be moieties that comprise one or more functional groups and/or carbon chains independently comprising esters, carbonyls, isocyanates, carbonyl amides, sulfonamides, sulfonates, ethers, and combinations thereof. In certain embodiments, the carbonyl amides may comprise a urea or urethane.

In a third embodiment, the present disclosure may provide a method according to any one of the first and second embodiments, wherein M is $R^3R^4N^+$.

In a fourth embodiment, the present disclosure may provide a method according to the third embodiment, wherein M is associated with an anion such that the LDHI compound has the structural formula:

In a fifth embodiment, the present disclosure may provide a method according to the fourth embodiment, wherein the LDHI compound has the structural formula:

In a sixth embodiment, the present disclosure may provide a method according to any one of the third and fifth embodiments, wherein $R^3$ is a $C_4$ to $C_8$ hydrocarbon chain and further wherein $R^4$ is hydrogen.

In a seventh embodiment, the present disclosure may provide a method according to any one of the foregoing embodiments, wherein each of $R^1$ and $R^2$ is a $C_8$ to $C_{18}$ hydrocarbon chain.

In an eighth embodiment, the present disclosure may provide a method according to any one of the foregoing embodiments, wherein the fluid resides within a conduit.

In a ninth embodiment, the present disclosure may provide a method according to any one of the foregoing embodiments, wherein the fluid has a water cut of about 30% to about 50%.

In a tenth embodiment, the present disclosure may provide a method according to any one of the foregoing embodiments, wherein the composition is introduced in an amount such that the LDHI compound is present in the fluid in an amount equal to about 0.1 to about 3.0% volume based on water cut of the fluid.

In an eleventh embodiment, the present disclosure may provide a method of inhibiting the formation of hydrate agglomerates, the method comprising: introducing a composition into a fluid comprising (i) water and (ii) one of gas, liquid hydrocarbon, and combinations thereof, wherein the composition comprises an LDHI compound comprising multiple lipophilic tails, a linking moiety, and an ammonium hydrophilic head comprising a quaternary ammonium cation having the structural formula:

wherein each of R³ and R⁴ is independently selected from the group consisting of hydrogen and a $C_1$ to $C_{10}$ hydrocarbon chain.

In a twelfth embodiment, the present disclosure may provide a method according to the eleventh embodiment, wherein each lipophilic tail is independently a $C_8$ to $C_{18}$ hydrocarbon chain.

In a thirteenth embodiment, the present disclosure may provide a method according to any one of the eleventh and twelfth embodiments, wherein the composition is introduced in an amount such that the LDHI compound is present in the fluid in an amount equal to about 0.1 to about 3.0% volume based on water cut of the fluid.

In a fourteenth embodiment, the present disclosure may provide a method according to any one of the eleventh-thirteenth embodiments, wherein the fluid resides within a conduit.

In a fifteenth embodiment, the present disclosure may provide a method according to any one of the foregoing embodiments, wherein the LDHI compound comprises the reaction product of a reaction between (i) an amide intermediate resulting from a reaction between diethylenetriamine (DETA) and one or more fatty acids; and (ii) alkyl halide.

In a sixteenth embodiment, the present disclosure may provide a method according to the 15th embodiment, wherein the one or more fatty acids comprises a fatty acid selected from the group consisting of: corn oil, canola oil, and combinations thereof.

In a seventeenth embodiment, the present disclosure may provide a method according to any one of the foregoing embodiments, wherein the fluid resides within a subterranean formation.

In an eighteenth embodiment, the present disclosure may provide a compound having the structural formula wherein each of R¹ and R² is a $C_1$ to $C_{50}$ hydrocarbon chain; R³ is a $C_1$ to $C_{10}$ hydrocarbon chain; and X is an anion selected from the group consisting of halide, carboxylate, sulfate, organic sulfonate, hydroxide, and combinations thereof.

In a nineteenth embodiment, the present disclosure may provide a compound according to the eighteenth embodiment, wherein each of R¹ and R² is a $C_1$ to $C_{50}$ hydrocarbon chain resulting from reaction between an amine having structure $H_2N$—$CH_2$—$NH$—$CH_2$—$NH_2$ and a fatty acid, the fatty acid being selected from the group consisting of: corn oil and canola oil.

In a twentieth embodiment, the present disclosure may provide a composition comprising a compound having the structural formula wherein each of R¹ and R² is a $C_1$ to $C_{50}$ hydrocarbon chain; R³ is a $C_1$ to $C_{10}$ hydrocarbon chain; and X is an anion selected from the group consisting of halide, carboxylate, sulfate, organic sulfonate, hydroxide, and combinations thereof.

In a twenty-first embodiment, the present disclosure may provide a composition according to the twentieth embodiment, wherein each of R¹ and R² is a $C_1$ to $C_{50}$ hydrocarbon chain resulting from reaction between an amine having structure $H_2N$—$CH_2$—$NH$—$CH_2$—$NH_2$ and a fatty acid, the fatty acid being selected from the group consisting of: corn oil and canola oil.

In a twenty-second embodiment, the present disclosure may provide a composition according to the twentieth embodiment, further comprising a solvent selected from the group consisting of: toluene, xylene, methanol, isopropyl alcohol, glycol, and combinations thereof.

To facilitate a better understanding of the present disclosure, the following example according to some of the embodiments is given. In no way should such example be read to limit the scope of the invention.

EXAMPLE

A. Methodology

Rocking cell tests were carried out on numerous samples of different compounds having structures according to some embodiments of the present disclosure. Rocking cell tests involve injection of oil, water, and LDHI compound into a cell at representative conditions. Optionally, additional gas may be injected into the cell (e.g., to achieve a desired working pressure during the experiment). Each cell was of a fixed volume and contained constant mass during the experiment; that is, oil, water, LDHI compound, and (in some cases) gas were injected at the beginning of the experiment, but thereafter the cell was closed to mass transfer in or out of the cell. Each cell also included a magnetic ball in the space where fluids are injected. The ball aided in agitation of the fluids during rocking. In addition, magnetic sensors on both ends of the cell detected whether the magnetic ball's movements through the fluids were hindered during rocking, thereby indicating the presence of hydrates. The cell also permitted visual observation of its contents for formation of hydrates during the experiment.

Initially, amounts of oil, water, and LDHI compound were injected into the cell so as to achieve the desired water cut (i.e., fraction of aqueous phase in the total fluid) and LDHI compound dosage (volume % of LDHI compound on water cut basis) of the experiment. As performed in this instance, three different water cuts were used in each of 3 different test runs for each sample: 30%, 40%, and 50%. Dosage for LDHI compounds in all tests was 2.0% volume on water cut basis. After injection of oil, water, and LDHI compound, gas was injected to reach a desired pressure (e.g., working pressure of a conduit of interest for evaluation of the LDHI compound, in this case around 2,000 psi). Gas composition varied based upon the conditions that would be encountered in the target conduit for the LDHI compound.

Following injection of the gas, the cell was closed and rocked for approximately 2 hours to emulsify the fluids therein. Temperature is then ramped down from 20° C. to 4° C. over a period of about 2 hours, and rocking is continued for around 14 hours after the temperature reaches final temperature. The rocking is then stopped for a period of time while the cell is horizontal (e.g., to simulate a system shut-in). This "shut-in" period lasts for at least 6 hours, varying only so that the re-start of rocking could be visually observed. Visual observations of the contents of the cell are made throughout the tests, with particular attention paid to the following three phases of the test: (1) initial cooling period; (2) pre-shut-in; and (3) restart following shut-in. These three phases of the testing provide a basis for visual rating of the performance of the LDHI compound as a hydrate inhibitor. Visual ranking results in a score at each phase, based upon a scale of 1 through 5 according to the criteria set forth in Table 1 below. For systems with dark oils additional confirmation may be required via the signal from the magnetic proximity sensors' detection of movement of the magnetic ball.

TABLE 1

Rocking Cell Visual Rating Criteria for LDHI Hydrate Inhibitors

| Grade | Description |
|---|---|
| 5 | No or Ultra-fine Hydrate Crystals; Fully Flowable System |
|   | No visible deposits on cell body or sapphire window. |
|   | Full liquid level. |
|   | Single phase or multiple, easily dispersible phases (i.e., brine, oil & hydrates). |
|   | Low viscosity liquid(s). |
|   | Ultra-fine hydrate crystal particle size (if present; hydrates may look like 'milk'). |
| 4 | Larger Hydrate Particles and/or More Viscous Liquid than Grade 5; Flowable System |
|   | Small quantities of intermittent visible deposits on cell body or sapphire window |
|   | Full liquid level. |
|   | Single phase or multiple, easily dispersible phases (i.e., brine, oil & hydrates). |
|   | Low liquid viscosity. |
|   | Fine hydrate crystal particle size if present (≤2 mm). |
|   | Weak hydrate crystal association if present. |
| 3 | System will Flow with Difficulty |
|   | Intermittent visible deposits on cell body or sapphire window |
|   | Full liquid level. |
|   | Liquid is viscous and slowly dispersible. |
|   | Intermediate liquid viscosity. |
|   | Fine hydrate crystal particles (≤2 mm). |
|   | No large crystals |
| 2 | System will Most Likely Plug |
|   | Visible deposits on cell body or sapphire window |
|   | Full or low liquid level. |
|   | Visible hydrate crystal deposits. |
|   | Stuck ball. |
|   | Large solid crystals (>3 mm) may break with strong agitation. |
| 1 | System will Plug |
|   | Visible deposits on cell body or sapphire window |
|   | Low liquid level. |
|   | Stuck ball. |
|   | Two phases, one will disperse. |
|   | Exceedingly high liquid viscosity. |
|   | Large agglomerations (>3 mm). |
|   | Large solid crystals do not break with strong agitation. |

B. Testing of Particular LDHI Compound Samples

Samples were prepared including compounds with structures according to some embodiments of the present disclosure. Samples prepared had the following base structure:

Each sample had $R^1$ and $R^3$ as defined in Table 2 below. In instances where $R^1$ varied within a molecule of the compound and/or from one molecule to another of the compound, the reactant fatty acid is instead listed (e.g., as in the case of Samples 1 and 2).

TABLE 2

Sample Multi-Tail LDHI Hydrate Inhibitors

| Samples No. | R1 | R3 | X⁻ | Dose % | Water Cut 30% | Water Cut 40% | Water Cut 50% |
|---|---|---|---|---|---|---|---|
| 1 | Corn Oil | $C_5H_{11}$ | Br⁻ | 2.0% | 3-5 | 3-5 | 1-2 |
| 2 | Canola Oil | $C_5H_{11}$ | Br⁻ | 2.0% | 3-5 | 3-5 | 3-5 |
| 3 | $C_{18}H_{37}$ | $C_4H_9$ | Br⁻ | 2.0% | 1-2 | — | — |
| 4 | $C_{18}H_{37}$ | $C_5H_{11}$ | Br⁻ | 2.0% | 3-5 | 1-2 | — |
| 5 | $C_{18}H_{37}$ | $C_6H_{13}$ | Br⁻ | 2.0% | 1-2 | — | — |
| 6 | $C_{18}H_{37}$ | $C_7H_7$(Benzyl) | Br⁻ | 2.0% | 1-2 | — | — |
| 7 | $C_{18}H_{37}$ | $C_8H_{17}$ | Br⁻ | 2.0% | 1-2 | — | — |
| 8 | $C_{12}H_{25}$ | $C_4H_9$ | Br⁻ | 2.0% | 3-5 | 3-5 | 3-5 |
| 9 | $C_{12}H_{25}$ | $C_5H_{11}$ | Br⁻ | 2.0% | 3-5 | 1-2 | — |
| 10 | $C_{12}H_{25}$ | $C_6H_{13}$ | Br⁻ | 2.0% | 1-2 | — | — |
| 11 | $C_{12}H_{25}$ | $C_7H_7$(Benzyl) | Br⁻ | 2.0% | 3-5 | 1-2 | — |
| 12 | $C_{12}H_{25}$ | $C_8H_{17}$ | Br⁻ | 2.0% | 1-2 | — | — |
| 13 | $C_8H_{17}$ | $C_4H_9$ | Br⁻ | 2.0% | 1-2 | — | — |
| 14 | $C_8H_{17}$ | $C_5H_{11}$ | Br⁻ | 2.0% | 1-2 | — | — |
| 15 | $C_8H_{17}$ | $C_6H_{13}$ | Br⁻ | 2.0% | 1-2 | — | — |
| 16 | $C_8H_{17}$ | $C_7H_7$(Benzyl) | Br⁻ | 2.0% | 1-2 | — | — |
| 17 | $C_8H_{17}$ | $C_8H_{17}$ | Br⁻ | 2.0% | 1-2 | — | — |

As also indicated by Table 2, each sample was applied at the indicated dosage (2.0% v/v based on water cut) to fluids having one or more of 3 different water cuts: 30%, 40%, and 50%. Where no grade is indicated for a water cut in Table 2, no test at that water cut was performed for the corresponding sample. In general, samples that obtained a score of 3-5 at 30% water cut were then tested at 40% water cut, and samples obtaining a score of 3-5 at 40% were then tested at 50% water cut. As shown by Table 2, Samples 2 (prepared from canola oil) and 8 (having a $C_{12}$ hydrocarbon chain of form $C_{12}H$) presented the best results, with scores of 3-5 at all three water cuts tested. This is followed by Sample 1, prepared from corn oil, having a score in the 3-5 range at both the 30% and 40% water cut tests, but a 1-2 range score in the 50% water cut test.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. In particular, every range of values (of the form, "from about a to about b," or, equivalently, "from approximately a to b," or, equivalently, "from approximately a-b") disclosed herein is to be understood as referring to the power set (the set of all subsets) of the respective range of values, and set forth every range encompassed within the broader range of values. Also, the terms in the claims have their plain, ordinary meaning unless otherwise explicitly and clearly defined by the patentee.

What is claimed is:

1. A method of inhibiting the formation of hydrate agglomerates, the method comprising:
   introducing a composition into a fluid comprising (i) water and (ii) one of gas, liquid hydrocarbon, and any combination thereof;
   wherein the composition comprises a low-dosage hydrate inhibitor ("LDHI") compound comprising multiple lipophilic tails, a linking moiety, and an ammonium hydrophilic head comprising a quaternary ammonium cation moiety, and wherein the LDHI compound has the structural formula:

wherein each of $R^1$ and $R^2$ is a $C_1$ to $C_{50}$ hydrocarbon chain;
wherein each of Z and Z' is a moiety comprising a functional group that comprises at least one carbon;
wherein each of L and L' is a $C_1$ to $C_{20}$ hydrocarbon chain;
wherein each of $R^3$ and $R^4$ is independently selected from the group consisting of: hydrogen and a $C_1$ to $C_{10}$ hydrocarbon chain; and
wherein $R^3R^4N^+$ is associated with an anion $X^-$, wherein the $X^-$ comprises an anion selected from a group consisting of: a bromide, a carboxylate, an organic sulfonate, a hydroxide, and any combination thereof.

2. The method of claim 1, wherein the composition is introduced in an amount such that the LDHI compound is present in the fluid in an amount equal to about 0.1 to about 3.0% volume based on water cut of the fluid.

3. The method of claim 2, wherein the fluid resides within a conduit.

4. The method of claim 2, wherein the fluid resides within a subterranean formation.

5. The method of claim 1, wherein the fluid has a water cut of about 30% to about 50%.

6. The method of claim 1, wherein the LDHI compound comprises the reaction product of a reaction between (i) an amide intermediate resulting from a reaction between diethylenetriamine (DETA) and one or more fatty acids; and (ii) alkyl halide.

7. The method of claim 6, wherein the one or more fatty acids comprises a fatty acid selected from the group consisting of: corn oil, canola oil, and any combination thereof.

8. The method of claim 1, wherein each lipophilic tail is independently a $C_8$ to $C_{18}$ hydrocarbon chain.

9. The method of claim 1, wherein Z and Z' are carbonyl groups, L and L' are $C_2$ hydrocarbon chains, and the LDHI compound has the structural formula:

10. The method of claim 1, wherein $R^3$ is a $C_4$ to $C_8$ hydrocarbon chain, and $R^4$ is hydrogen.

11. The method of claim 1, wherein the fluid further comprises a solvent selected from the group consisting of: toluene, xylene, methanol, isopropyl alcohol, glycol, and combinations thereof.

* * * * *